United States Patent [19]

O'Connor

[11] Patent Number: 4,956,118
[45] Date of Patent: Sep. 11, 1990

[54] LUBRICATING COMPOSITION CONTAINING ANTI-WEAR/EXTREME PRESSURE ADDITIVES

[75] Inventor: Sean P. O'Connor, Beverley, England

[73] Assignee: BP Chemicals Limited, London, England

[21] Appl. No.: 195,099

[22] Filed: May 17, 1988

[30] Foreign Application Priority Data

Jun. 2, 1987 [GB] United Kingdom ................. 8712931

[51] Int. Cl.$^5$ ........................................... C10M 133/40
[52] U.S. Cl. ..................................... 544/240; 252/47
[58] Field of Search ........................... 544/245; 252/47

[56] References Cited

U.S. PATENT DOCUMENTS

| | | | |
|---|---|---|---|
| 2,858,311 | 10/1958 | Steck | 544/240 |
| 2,905,672 | 9/1959 | Steck | 544/240 |
| 4,840,741 | 6/1989 | Beltzer et al. | 252/47 |

OTHER PUBLICATIONS

Chemical Abstracts 110(18) 157493a.

Primary Examiner—Jacqueline V. Howard
Attorney, Agent, or Firm—Brooks Haidt Haffner & Delahunty

[57] ABSTRACT

Compounds suitable for use as extreme pressure (EP)-/anti-wear (AW) agents in lubricating oil compositions, which compounds have the formula:

$$R^1—S—X—S—S—R \qquad (I)$$

wherein $R^1$ is either R—S— or hydrogen,

R is independently either hydrocarbyl or substituted hydrocarbyl, and

X comprises a heterocyclic ring having six atoms of which two are nitrogen atoms.

1 Claim, No Drawings

LUBRICATING COMPOSITION CONTAINING ANTI-WEAR/EXTREME PRESSURE ADDITIVES

The present invention relates to novel compounds suitable for use as anti-wear/anti-corrosion additives in lubricating oil compositions, to a method for their preparation and to lubricating oil compositions containing the aforesaid additives.

The severe demands placed upon lubricating oils by modern internal combustion engines necessitate incorporation into the lubricating oil of additives of various types, for example viscosity index improvers, dispersants, detergents, anti-oxidants, anti-wear (A.W.) agents, extreme pressure (E.P.) agents, and the like. Generally, each additive agent is employed to impart a particular characteristic to the base oil so as to afford a finished lubricating oil composition which is oxidation resistant, stable and non-corrosive to bearing metals, and which effectively reduces varnish and sludge forming tendencies and minimises frictional and corrosive wear.

The use of zinc dialkyl dithiophosphates (ZDTPs) as additives in lubricating oils for the purpose of improving the wear and corrosion characteristics of the oil has long been known from, for example GB Patent Nos. 957,017: 1,358,478 and 1,565,961.

Despite the fact that ZDTPs have been very effective and very successful in a number of engine lubricating oils, it is presently considered desirable to reduce the phosphorus content of the finished lubricating oil by the provision of alternative additives for the purpose of reducing environmental pollution.

One class of compound proposed for this purpose are the hydrocarbon polysulphide derivatives of 2,5-dimercapto-1,3,4-thiadiazole having the general formula:

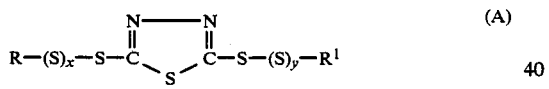

(A)

wherein R and $R^1$ are the same or different hydrocarbon radicals, x and y are numbers 0 to about 8, the sum of x and y is at least one, and preferably 2 to about 16. Such compounds are described in U.S. Pat. Nos. 2,719,125: 2,719,126 and 3,663,561. One of these compounds of formula:

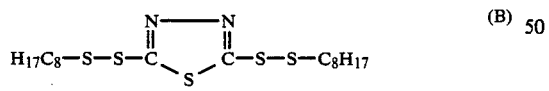

(B)

has achieved some commercial importance.

From DT-A-2814458 are also known lubricant compositions containing a 1,2,4-triazole derivative of the formula:

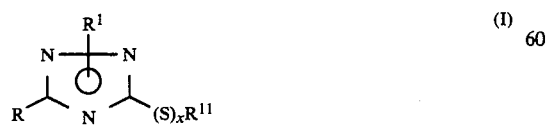

(I)

wherein
x = 1-25,
R, $R^1$ and $R^{11}$ are H, optionally substituted 1-20 C alkyl, 2-12 C alkenyl or alkynyl, optionally substituted 3-12 C cycloalkyl, optionally substituted 6-10 C aryl, optionally substituted 8-12 C aralkenyl or aralkynyl, optionally substituted 7-20 C aralkyl, optionally substituted 3-10 membered heterocyclyl, 2-12 C alkylene, 5-12 C cycloalkylene or 6-10 C arylene, or R can be $-(S)_xR^{11}$, or $R^{11}$ can be a heterocyclylthio group or an optionally substituted ammonium cation; when $R^{11}=H$, R or $R^1$ can also be an organic group linking 2 triazole residues of formula (I) with $R^1$ in the 4-position.

We have now found a class of novel compounds useful for the aforesaid purpose.

Accordingly, the present invention provides compounds suitable for use as EP/AW agents in lubricating oil compositions which compounds have the formula:

$$R^1-S-X-S-S-R \quad (I)$$

wherein
$R^1$ is either R—S— or hydrogen,
R is independently either hydrocarbyl or substituted hydrocarbyl, and
X comprises a heterocyclic ring having six atoms of which two are nitrogen atoms.

Preferred compounds of formula (I) are those in which $R^1$ is the group R—S—, i.e. compounds of the formula:

A preferred class of compounds conforming with the formula (I) are pyridazines having the formula:

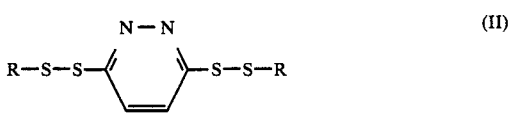

(II)

Another preferred class of compounds conforming with the formula (I) are pyrimidines having the formula,

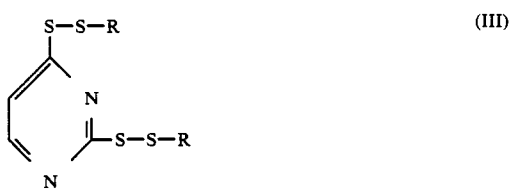

(III)

Yet another preferred class of compounds conforming with the formula (I) are pyrazines having the formula:

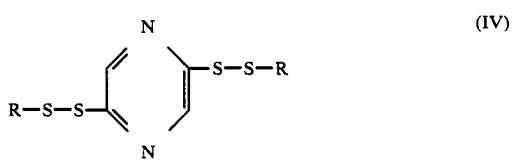

(IV)

Alternatively, the group X may be a fused ring heterocyclic group, for example a phthalazine or quinoxaline, typically a compound of the formula,

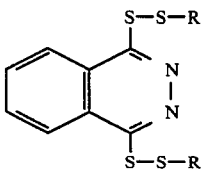 (V)

Furthermore, the ring(s) may be substituted.

The groups R in the formula (I) to (IV) are independently either hydrocarbyl or substituted hydrocarbyl groups. Suitable hydrocarbyl groups include alkyl and alkaryl groups and particularly alkyl groups containing sufficient carbon atoms to impart oil solubility, for example at least 4 carbon atoms, typically n-octyl or n-dodecyl groups. Suitable substituents in the substituted hydrocarbyl groups include hydroxy, alkoxy, acid, amido, amino and ester groups.

The present invention also provides a process for the production of compounds having the formula (I) which process comprises the steps of:

(A) reacting a thiol of the formula RSH (VI) wherein R is the same as in the formula (I) with thiourea and hydrogen peroxide in aqueous alcoholic media in the presence of a salt-forming acid to produce a salt of the formula:

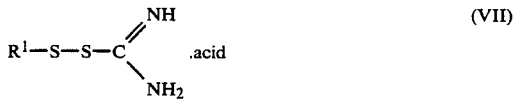 (VII)

(B) reacting the salt of formula (VII) with a compound of the formula:

 (VIII)

wherein X is the same as in the formula (I) in aqueous alcoholic media under basic conditions to produce the compound of formula (I), and (C) recovering the compound of formula (I) produced in step (B).

In step (A) of the process there is employed an alcohol. Suitable alcohols include aliphatic and aromatic alcohols, alcohol ethers, polyols, and the like. Preferably the alcohol is a $C_1$ to $C_4$ alkanol, for example methanol or ethanol. The acid may suitably be any acid which forms an acid salt, and may be either a mineral or organic acid, preferably a mineral acid. Suitable acids are those of the formula HX wherein X is halide, for example chloride. Step (A) may suitably be carried out at sub-ambient, ambient or elevated temperature, preferably at a temperature in the range 0° to 25° C.

In step (B) of the process there is employed an alcohol, which may be the same or different to the alcohol employed in step (A). The reaction is carried out under basic conditions, which may be accomplished by addition of an organic or inorganic base, preferably an inorganic base, for example sodium bicarbonate. The reaction may suitably be carried out at sub-ambient, ambient or elevated temperature, preferably in the range from 0° C. to the reflux temperature of the alcohol. In order to form the compound of formula (I) wherein $R^1$ is R—S— it will be generally necessary to use about 2 moles of the salt of formula VII, whereas to form the compound of formula (I) wherein $R^1$=H only one mole will generally be required.

In step (C) the compound of formula (I) is recovered. This may be accomplished in conventional manner.

The present invention also provides a finished lubricating oil composition comprising a lubricating oil base stock and an EP/AW-improving amount of a compound of the formula (I).

The lubricating oil base stock may be any oil of lubricating viscosity, which may be a mineral oil or a synthetic lubricating oil. Suitable mineral oils include both solvent extracted or solvent refined oils obtained in accordance with conventional methods of treating lubricating oils. The base oil may be derived from paraffinic, naphthenic, asphaltic or mixed base crudes. Alternatively, the base oil may be a synthetic oil, or a mixture thereof with mineral oil.

The lubricating oil composition may suitably contain from 0.01 to 10, preferably from 0.1 to 1% w/w of the compound of formula (I), the remainder of the composition being comprised of the lubricating oil base stock.

In addition, the lubricating oil composition may contain conventional additives, for example dispersants, detergents, VI improvers, anti-oxidants, pour-point depressants, or the like.

Lubricating oil additives are generally manufactured and marketed in the form of a concentrate for subsequent blending into finished lubricating oils.

In another embodiment of the invention there is provided a lubricating oil additive concentrate for use in the production of finished lubricating oils which comprises a lubricating oil base stock and sufficient of a compound of formula (I) to give a concentration of from 0.01 to 10, preferably from 0.1 to 1%, w/w in the finished lubricating oil composition.

Suitably the concentration of the compound of formula (I) in the concentrate composition may be from 2 to 20, typically about 10, times its concentration in the finished lubricating oil composition.

The lubricating oil base stock may be any of the aforedescribed lubricating oils, but is preferably a solvent neutral oil. As an alternative to incorporating conventional additives directly in the finished lubricating oil, some or all of the additives may be incorporated into the concentrate composition.

The invention will now be further illustrated by reference to the following examples.

PREPARATION OF COMPOUNDS OF THE FORMULA (I)

Preparation of pyrimidine-2,4-dithiol [formula (VII)] for use in step (B) of the process A suspension of 2-thiouracil (32.0 g, 0.25 mole) in pyridine (150 ml) was stirred at room temperature and treated portionwise with phosphorus pentasulphide (21.25 g) over 40 minutes. The reaction mixture was then refluxed for 45 minutes giving a homogeneous solution which was then cooled and treated with iced water (250 ml) and the resultant mixture stirred at 80°-90° C. for 2 hours during which time hydrogen sulphide was evolved and a solid formed. The mixture was cooled and acidified with conc. hydrochloric acid and filtered. The solid was washed thoroughly with water and dried giving the dithiol as a yellow powder (28.6 g; 79%). The product was analysed for sulphur content with the following result:

Analysis
Sulphur: Found 44.0%;
Calculated 44.47%.

Preparation of Phthalazine-1,4-dithiol [Formula (VII)] for Use in Step (B) of the Process A stirred suspension of phthalhydrazide (40.5 g, 0.25 mole) in pyridine (150 ml) was treated portionwise over 1 hour with phosphorus pentasulphide (42.5 g) at room temperature (15° C.). The temperature of the mixture was observed to rise to 40° C. during the addition. The mixture was then refluxed and stirred for 20 hours. It was then cooled to 15° C., treated with iced-water (250 ml) and stirred at 80°-90° C. for 2 hours. The mixture was cooled, acidified (concentrated hydrochloric acid) and filtered. The solid was washed thoroughly with water and dried giving the product as a yellow solid (45.2 g, 93%).

Example 1

Step (A)—Preparation of S-n-octylthioisothiourea hydrochloride [formula (VI)] for Use in Step (B) of the Process Hydrogen peroxide (30% aqueous, 28.0 g) was added dropwise over 45 minutes to a stirred mixture of n-octanethiol (32.27 g, 0.221 mole), thiourea (20.1 g, 0.264 mole), concentrated hydrochloric acid (35 ml), water (35 ml) and ethanol (500 ml) maintained at 0°-10° C. After the addition was complete the reaction mixture was stirred at room temperature for 2 hours during which time a thick white precipitate formed. The mixture was filtered and the filtrate evaporated giving a solid residue. This was dissolved in ethanol (150 ml), diluted with diethyl ether (800 ml) and allowed to stand overnight at 0° C. Filtration gave white crystals of the product (46.3 g; 82%), melting point=77°-82° C.

Steps (B) and (C)—Preparation and recovery of 2,4-bis(n-octyldithio) pyrimidine [formula (III)]

A solution of sodium bicarbonate (4.30 g; 0.05 mole) in water (60 ml) was added dropwise to a stirred suspension of pyrimidine-2,4-dithiol prepared as above (2.16 g, 0.015 mole) and S-n-octylthioisothiourea hydrochloride obtained in step (A) (7.695 g, 0.03 mole) in methanol (70 ml) at 60°-65° C. over 30 minutes. The mixture was stirred at room temperature for a further hour and then extracted into naphtha (3×50 ml). The organic extracts were washed with water, dried using anhydrous MgSO4 and evaporated yielding the product as an orange oil (5.54 g; 85%).

Examples 2 and 3

The following compounds of the formula (I) were prepared by the procedure described in Example 1 except that a pyridazine dithiol prepared in a similar manner to the pyrimidine dithiol was used in place of the pyrimidine dithiol:
Example 2—with reference to formula (II), R=n-octyl.
Example 3—with reference to formula (II), R=n-dodecyl.

Example 4

Step (A)—Preparation of S-n-octylthioisothiourea Hydrochloride [formula (VI) for Use in Step (B) of the Process The procedure of Example 1 was repeated.

Steps (B) and (C)—Preparation and Recovery of 1,4-bis (n-octyldithio)phthalazine [formula V)]

A solution of sodium bicarbonate (4.30 8, 0.05 mole) in water (60 ml) was added dropwise to a stirred suspension of the phthalazine-1,4-diol prepared as above (2.91 g, 0.015 mole) and S-n-octylthioisothiourea obtained in step (A) (7.695 g, 0.03 mole) in methanol (70 ml) at 60°-65° C. over 30 minutes. The mixture was stirred at room temperature for a further hour, then filtered giving a yellow solid, which was washed with water and dried giving the duct as yellow crystals (6.56 g, 91%).

COMPARISON TESTS A AND B 2,5-dithioalkyl,1,3,4-thiadiazoles of the formula (A) in which $R=R^1=$n-octyl and $x=y=1$ (Comparison Test A) and in which $R=R^1=$n-dodecyl (Comparison Test B) and $x=y=1$ were prepared by the method of Example 1, Steps B and C starting from 2,5-dimercapto-1,3,4-thiadiazole and the appropriate S-n-alkylthioiso-thiourea hydrochloride.

These are not examples of compounds according to the present invention and were prepared for comparison purposes only.

The identities of the substituents (with reference to the formula (I)) and the melting points (where applicable) of the products of Examples 1-4 and Comparison Tests A and B are given in Table 1.

table 1

| Example | X (Heterocycle) | R | M Pt (°C.) |
|---|---|---|---|
| 1 | pyrimidine | n-octyl | oil |
| 2 | pyridazine | n-octyl | 58-61 |
| 3 | pyridazine | n-dodecyl | 81-84 |
| 4 | phthalazine | n-octyl | 61-64 |
| Comp Test A | 1,3,4-thiadiazole | n-octyl | oil |
| Comp Test B | 1,3,4-thiadiazole | n-dodecyl | 31-34 |

PRODUCT TESTING

Example 5

A blend of the product of Example 2 was made up in SN 150 base oil at a concentration of 0.1% and the anti-wear properties of the blend were tested using the Shell four-ball test. This test involved passing a rotating steel ball against a triangle of three stationary balls lubricated with the blend under test. The Initial Seizure Load (ISL), the scar diameter (40 kg/one hour) and the Weld Load (WL) were determined.

The copper strip rating of the blend was also determined at 150° C. after 3 hours in conventional manner.

Example 5

The procedure of Example 4 was repeated except that the 1,4-bis(n-octyldithio)phthalazine of Example 4 was used instead of the pyridazine of Example 2.

The results are given in Table 2.

Comparison Test C

The procedure of Example 5 was used except that no additive was employed.

Comparison Test D

The procedure of Example 5 was employed except that instead of the compound of formula (I) there was used the 1,3,4-thiadiazole of Comparison Test A.

Comparison Test E

The procedure of Example 5 was used except that instead of the compound of formula (I) there was used a commercially available thiadiazole ashless EP/AW agent.

Comparison Tests F and G

The procedure of Example 5 was used except that instead of the compound of formula (I) there was used different commercially available zinc dialkyl dithiophosphates (1) and (2).

Comparison Tests C to G are not examples according to the present invention because no compound of the formula (I) was employed. They are included only for the purpose of comparison.

The results of the four-ball tests and the copper strip rating determinations are given in Table 2.

Comparison Test C

The procedure of Example 5 was used except that no additive was employed.

TABLE 2

| Example | Product | Concn (%) | Four-ball test ISL | | | Copper strip rating 150° C./ 3 hours |
|---|---|---|---|---|---|---|
| | | | kg | scar (mm) | WL kg | |
| Comp Test C | SM 150 | — | 40 | 1.30 | 120 cat | 3A |
| Comp Test D | Comp Test A (thiadiazole) | 0.1 | 60 | 1.57 | 170 | 2D |
| Comp Test E | commercial thiadiazole | 0.1 | 70 | 1.70 | 160 | 3A |
| 5 | Example 2 | 0.1 | 60 | 1.68 | 160 cat | 3A |
| 6 | Example 4 | 0.1 | 50 | 1.55 | 160 | 2C |

TABLE 2-continued

| Example | Product | Concn (%) | Four-ball test ISL | | | Copper strip rating 150° C./ 3 hours |
|---|---|---|---|---|---|---|
| | | | kg | scar (mm) | WL kg | |
| Comp Test F | ZDTP (1) | 0.1 | 40 | 1.50 | 130 cat | 3A (1%) |
| Comp Test G | ZDTP (2) | 0.1 | 55 | 1.90 | 150 cat | 3A (1%) |

With reference to the Table:
cat—indicates catastrophic wear at this load

Copper Strip Ratings 1A-1B—Slight tarnish
2A-2E—Moderate tarnish
3A-3B—Dark tarnish
4A-4C—Corrosion The results shown in Table 2 demonstrate that compounds according to the invention are superior to the commercial ZDTPs tested and are comparable with their thiadiazole analogues in terms of EP/AW and corrosion properties at the concentrations used.

I claim:

1. Compounds suitable for use as extreme pressure (EP)/anti-wear (AW) agents in lubricating oil compositions, which are pyridazines having the formula:

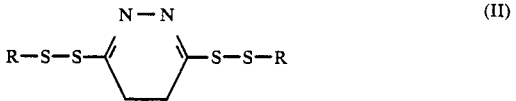

wherein R is independently either hydrocarbyl or substituted hydrocarbyl.

* * * * *

UNITED STATES PATENT AND TRADEMARK OFFICE
CERTIFICATE OF CORRECTION

PATENT NO. : 4,956,118

DATED : September 11, 1990

INVENTOR(S) : SEAN P. O'CONNOR

It is certified that error appears in the above-identified patent and that said Letters Patent is hereby corrected as shown below:

Col. 1, l. 46, there should be a semicolon after "2,719,125;"

Col. 2, l. 68, there should be a colon (:) after the word "formula:"

Col. 3, l. 52, correct the spelling of the word "example"

Col. 4, l. 67, there should be no semicolon after "44.0%"

Col. 6, l. 7, should read "giving the product as"

Col. 6, l. 18, correct spelling of the word "prepared"

Col. 7, Table 2, l. 28, "WL" should appear on the line above.

Col. 8, Table 2, l. 5, "WL" should appear on the line above.

Signed and Sealed this

Seventh Day of July, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,956,118
DATED : September 11, 1990
INVENTOR(S) : Sean P. O'Connor It is certified that error appears in the above-identified patent and that said Letters Patent is hereby corrected as shown below:

Title Page:

"[73]   Assignee: BP Chemicals Limited, London, England should read:

--[73]   Assignee: BP Chemicals (Additives) Limited, London, England.

Signed and Sealed this

Eleventh Day of August, 1992

Attest:

DOUGLAS B. COMER

*Attesting Officer*   *Acting Commissioner of Patents and Trademarks*